(12) United States Patent
Gadd et al.

(10) Patent No.: US 8,207,226 B1
(45) Date of Patent: Jun. 26, 2012

(54) USE OF FAAH ANTAGONISTS FOR TREATING DRY EYE AND OCULAR PAIN

(75) Inventors: Martha E. Gadd, Fort Worth, TX (US); Karen C. David, Masnfield, TX (US)

(73) Assignee: Alcon Research, Ltd., Fort Worth, TX (US)

(*) Notice: Subject to any disclaimer, the term of this patent is extended or adjusted under 35 U.S.C. 154(b) by 0 days.

(21) Appl. No.: 12/476,515

(22) Filed: Jun. 2, 2009

Related U.S. Application Data

(60) Provisional application No. 61/058,343, filed on Jun. 3, 2008.

(51) Int. Cl.
*A61K 31/195* (2006.01)
(52) U.S. Cl. ........................ 514/563; 514/912
(58) Field of Classification Search .................. 514/563, 514/912
See application file for complete search history.

(56) References Cited

U.S. PATENT DOCUMENTS

| | | | |
|---|---|---|---|
| 4,818,537 A | 4/1989 | Guo | |
| 4,939,135 A | 7/1990 | Robertson et al. | |
| 5,041,434 A | 8/1991 | Lubkin | |
| 5,290,572 A | 3/1994 | Macken | |
| 5,401,510 A | 3/1995 | Robertson et al. | |
| 5,696,166 A | 12/1997 | Yanni et al. | |
| 5,800,807 A | 9/1998 | Hu et al. | |
| 5,861,148 A * | 1/1999 | Smith | 424/78.04 |
| 5,958,912 A | 9/1999 | Sullivan | |
| 6,153,607 A | 11/2000 | Pflugfelder | |
| 6,462,054 B1 | 10/2002 | Boger | |
| 6,562,846 B2 | 5/2003 | Sit | |
| 6,949,574 B2 | 9/2005 | Sit | |
| 2002/0164769 A1 * | 11/2002 | Curtis et al. | 435/228 |
| 2008/0269325 A1 * | 10/2008 | Rice et al. | 514/515 |

FOREIGN PATENT DOCUMENTS

| | | |
|---|---|---|
| WO | 0003705 | 1/2000 |
| WO | 03065989 | 8/2003 |
| WO | 2004020430 | 3/2004 |
| WO | 2004033422 | 4/2004 |
| WO | 2005033066 | 4/2005 |

OTHER PUBLICATIONS

Boger et al., "Exceptionally potent inhibitors of fatty acid amide hydrolase: the enzyme responsible for degradation of endogenous oleamide and anandamide", PNAS, vol. 97, No. 10, pp. 5044-5049 (May 9, 2000).
Cravatt and Lichtman, "The enzymatic inactivation of the fatty acid amide class of signaling lipids", Chemistry and Physics of Lipids, vol. 121, pp. 135-148 (2002).
Jhaveri et al.; "Analgesic effects of fatty acid amide hydrolase inhibition in a rat model of neuropathic pain", The Journal of Neurosciences; vol. 26, No. 51, pp. 13318-13327 (Dec. 20, 2006).
Laine et al., "Effects of topical anandamide-transport inhibitors, AM404 and olvanil, on intraocular pressure in normotensive rabbits", Pharmaceutical Research, vol. 18, No. 4, (2001).
Lemp, "Report of the National Eye Institute/Industry Workshop on Clinical Trials in Dry Eyes", CLAO Journal, vol. 21, No. 4, pp. 221-231 (1995).
Marsh et al., "Topical nonpreserved methylprednisolone therapy for keratoconjunctivitis sicca in sjogren syndrome", Ophthalmology, vol. 106, pp. 811-816 (1999).
Matsuda et al., "Metabolism of anandamide, an endogenous cannabinoid receptor ligand, in porcine ocular tissues", Exp. Eye Res., vol. 64, pp. 707-711 (1997).
McCully and Shine, "Tear film structure and dry eye", Contactologia, vol. 20, No. 4, pp. 145-149 (1998).
Nichols et al., "Identification of fatty acids and fatty acid amides in human meibomian gland secretions", Investigative Ophthalmology & Visual Science, vol. 48, No. 1, pp. 34-39 (2007).
Piomelli et al., "Pharmacological profile of the selective FAAH inhibitor KBS-4103 (URB597), CNS Drug Reviews, vol. 12, No. 1, pp. 21-38 (2006).
Shine and McCulley, "Keratoconjunctivitis sicca associated with meibomian secretion polar lipid abnormality", Archives of Ophthalmology, vol. 116, No. 7, pp. 849-852 (1998).
Sit et al., "Novel inhibitors of fatty acid amide hydrolase", Bioorganic and Medicinal Chemistry Letters, vol. 17, pp. 3287-3291 (2007).
Tauber, "Lacrimal gland, tear film, and dry eye syndromes 2: Basic science and clinical relevance", Adv. Exp. Med. Biology, vol. 438, pp. 969-972 (1998).

* cited by examiner

*Primary Examiner* — Zohreh Fay
(74) *Attorney, Agent, or Firm* — Jason J. Derry

(57) ABSTRACT

Methods of treating symptoms of dry eye by administering a fatty acid amide or inhibitors of fatty acid amide hydrolase (FAAH) are disclosed. Methods of preventing or alleviating ocular pain by administering a fatty acid amide or FAAH inhibitors are also disclosed.

5 Claims, 1 Drawing Sheet

Nociception Test with Fatty Acid Amides
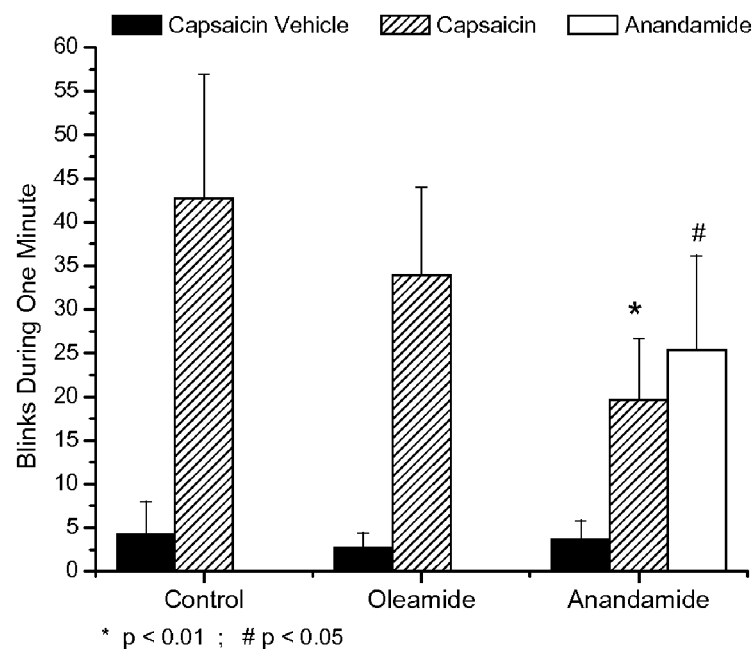

USE OF FAAH ANTAGONISTS FOR TREATING DRY EYE AND OCULAR PAIN

The present application claims the benefit of U.S. Provisional Patent Application Ser. No. 61/058,343, filed on Jun. 3, 2008, the disclosure of which is specifically incorporated by reference herein.

FIELD OF THE INVENTION

The invention relates to the treatment of ocular pain and symptoms of dry eye disorders. In particular, the invention relates to the use of certain fatty acid amide hydrolase (FAAH) inhibitors or a fatty acid amide in the treatment of chronic corneal pain and neuropathies associated with dry eye or other ocular disorders.

BACKGROUND OF THE INVENTION

Pain is a perceived nociceptive response to local stimuli in the body. The perception of pain at the level of the central nervous system requires the transmission of painful stimuli by peripheral sensory nerve fibers. Upon stimulation of tissue (i.e., thermal, mechanical or chemical), electro-chemical signals are transmitted from the sensory nerve endings to the spinal column, and hence to the brain where pain is perceived.

The cornea is highly innervated with sensory afferents which transmit various painful stimuli to the central nervous system. Pain conditions involving the eye, therefore, can arise in numerous instances, such as: foreign body stimulus, inflammation, dry eye syndrome, accidental trauma, surgical procedures and post-surgical recovery. For example, ocular pain can result from photorefractive keratotomy ("PRK"), a vision correcting, surgical procedure whereby a laser is used to shape the cornea. This process involves the photoablation of Bowman's membrane and the stromal levels of the cornea. As a result, the denuding of the nerve-containing epithelial layers of the cornea can cause some patients to experience pain following laser surgery until the epithelium regenerates.

Various therapies have been attempted for the alleviation of pain. The use of non-steroidal anti-inflammatory drugs (NSAIDs), such as diclofenac, have been developed to treat pain. These agents inhibit cyclooxygenase dependent prostaglandin synthesis. Prostaglandins can modulate pain perception at the level of the central nervous system and systemic administration of NSAIDs is known to provide analgesia. However, the use of NSAIDs can involve undesired side effects including gastrointestinal bleeding and kidney dysfunction.

Local anesthetics are another class of pain modulators that relieve pain by directly inhibiting nerve cellular function. One problem with local anesthetic therapy is that the anesthetics exhibit a short duration of action. Another problem with the use of local anesthetics is that their mechanism of action, non-specific membrane stabilization, can have the undesired coincident effect of also inhibiting biological functions of other cells, such as fibroblasts and surrounding neural cells. In addition, chronic use of topical ocular anesthetics is undesirable due to the potential for inadvertent, unperceived damage. Therefore, even though pain sensation can be abated with local anesthetic treatment, healing and normal function of the tissue may be significantly compromised. There is a need, therefore, to discover agents which potently and specifically inhibit the transmission of painful stimuli by sensory afferents, without local anesthetic activity, following topical ocular application.

In addition to treating ocular pain, local topical ocular application of anesthetics has been proposed to reduce or eliminate sensations on the ocular surface to treat the symptoms of dry eye. However, chronic use of local anesthetics is accompanied by toxic side effects.

Dry eye, also referred to as keratoconjunctivitis sicca, is a common ophthalmological disorder affecting millions of persons each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjögren's syndrome and cicatricial pemphigoid, may also lead to dry eye conditions. Transient symptoms of dry eye associated with refractive surgery have been reported to last in some cases from six weeks to six months or more following surgery.

Although it appears that dry eye may result from a number of unrelated pathogenic causes, all presentations of the complication share a common effect, that is the breakdown of the pre-ocular tear film, which results in exposure of the ocular surface, dehydration, and cytokine production resulting in many of the symptoms outlined above (Lemp, Report of the National Eye Institute/Industry Workshop on Clinical Trials in Dry Eyes, The CLAO Journal, volume 21, number 4, pages 221-231 (1995)).

Practitioners have taken several approaches to the treatment of dry eye. One common approach has been to supplement and stabilize the ocular tear film using so-called artificial tears instilled throughout the day. Other approaches include the use of ocular inserts that promote retention of tears (e.g., punctal plugs) or the stimulation of endogenous tear production.

Examples of the tear substitution approach include the use of buffered, isotonic saline solutions, aqueous solutions containing water soluble polymers that render the solutions more viscous and thus less easily shed by the eye. Tear film stabilization is also attempted by providing one or more components of the tear film such as phospholipids and oils. Phospholipid compositions have been shown to be useful in treating dry eye; see, e.g., McCulley and Shine, Tear film structure and dry eye, Contactologia, volume 20(4), pages 145-49 (1998); and Shine and McCulley, Keratoconjunctivitis sicca associated with meibomian secretion polar lipid abnormality, Archives of Ophthalmology, volume 116(7), pages 849-52 (1998).

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain, since the use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

Aside from efforts described above, which are directed primarily to the palliative alleviation of symptoms associated with dry eye, methods and compositions directed to treatment of the physiological conditions that cause such symptoms have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production.

Such efforts to treat the underlying causes of dry eye have focused on treating inflammation of the relevant ocular tissues and meibomian gland dysfunction. The use of various types of agents for such treatment of dry eye patients has been disclosed, including steroids (e.g., U.S. Pat. No. 5,958,912; Marsh et al., Topical nonpreserved methylprednisolone therapy for keratoconjunctivitis sicca in Sjögren's syndrome, Ophthalmology, 106(4): 811-816 (1999); and Pflugfelder et al., U.S. Pat. No. 6,153,607), cytokine release inhibitors (Yanni, J. M.; et. al. WO 00/03705 A1), cyclosporine A (Tauber, J. Adv. Exp. Med. Biol. 1998, 438 (Lacrimal Gland, Tear Film, and Dry Eye Syndromes 2), 969), and mucosecretatogues, such as 15-HETE (Yanni et. al., U.S. Pat. No. 5,696, 166).

Fatty acid amide hydrolase (FAAH) is a membrane protein that hydrolyzes the fatty acid amide (FAA) class of signaling lipids. FAA signaling pathways are involved in such physiological processes as sleep, pain, feeding, and locomotion (Cravatt et al., 2002, *Chemistry and Physics of Lipids* 121: 135-148). In addition, by using a defined extraction method along with electrospray mass spectrometry, Nichols et al. demonstrated that certain fatty acid amides are present in the eye. In particular, Nichols et al. found that oleamide, a fatty acid amide that induces sleep in animals and modulates pain perception, is the predominant component of human meibomian gland secretions (meibum) (Nichols et al., 2007, *Invest. Ophthalmol. Vis. Sci.* 48:34-39). Meibum, once spread as a thin oil layer over the aqueous tear film, helps prevent evaporation and maintain the stability of the tear film. Nichols et al. postulated that oleamide or the oleamide:oleic acid ratio may play a unique role in ocular surface diseases, such as dry eye, but did not suggest that any other particular fatty acids and amides are involved in such roles.

Furthermore, Matsuda et al. demonstrated that anandamide hydrolase, a fatty acid amide hydrolase (FAAH), is expressed in porcine ocular tissues, including the retina, lens, iris, choroid, and the lacrimal gland (Matsuda et al., 1997, *Exp. Eye Res.* 64:707-711). Matsuda et al., however, did not discuss the role of fatty acid amides or FAAH in dry eye or pain associated with ocular disorders.

While certain studies have implicated FAAH as a potential target for treating neurophysiological disorders and associated pain (Cravatt et al., 2002, *Chemistry and Physics of Lipids* 121:135-148; Jhaveri et al., 2006, *J. of Neurosci.* 26:13318-13327), such studies have not investigated a potential role for FAAH or modulators of FAAH in affecting chronic corneal pain or neuropathies associated with dry eye or other ocular disorders.

As discussed herein, modulation of FAAH and/or FAA levels in the eye can effectively reduce ocular pain and reduce symptoms of dry eye.

SUMMARY OF THE INVENTION

The invention provides methods for the treatment of dry eye symptoms, including symptoms of dry eye associated with refractive surgery such as LASIK surgery.

The invention also provides methods for the treatment of ocular pain and inflammation. According to the methods of the invention, fatty acid amide hydrolase (FAAH) antagonists or fatty acid amides are administered to a patient to prevent or alleviate chronic corneal pain and neuropathies associated with dry eye or other ocular disorders and or events, such as cataract surgery, LASIK, PRK, accidental trauma, cicatricial pemphigoid, and either idiopathic neuropathies or those coincident with diabetes, and Sjögren's syndrome.

According to certain methods of the invention, FAAH antagonists or fatty acid amides are administered to a patient suffering from dry eye or corneal pain. In certain aspects, the methods of the invention involve the administration of fatty acid amides (FAAs), FAA analogues, FAA derivatives, and/or lipoaminoacids that can modulate FAAH activity and lead to increased levels of FAAs at the ocular surface.

The FAAH antagonists or fatty acid amides are preferably administered topically to the eye.

Specific preferred embodiments of the invention will become evident from the following more detailed description of certain preferred embodiments and the claims.

BRIEF DESCRIPTION OF THE DRAWINGS

FIG. 1 is a graph representing the effects of oleamide and anandamide in a capsaicin blink test conducted on seven week old Sprague-Dawley rats.

DETAILED DESCRIPTION OF THE INVENTION

According to the invention, inhibitors of FAAH are administered to a patient suffering from dry eye. The compounds suitable for use in the present invention inhibit the activity of FAAH by binding to FAAH at the ocular surface of a patient, thereby reducing the perception of pain associated with dry eye. As provided herein, FAAH antagonists are beneficial in treating various ocular pain states and other conditions associated with neuropathic pain. In particular, FAAH antagonists can inhibit endogenous FAAH from hydrolyzing FAAs at the ocular surface.

According to the invention, FAAH antagonists are administered to a patient to prevent or ameliorate ocular pain associated with various stimuli. For example, the FAAH antagonists and compositions of the present invention may be used in treating pain arising from allergens, inflammation, trauma, dry eye, and/or foreign body sensation, such as from contact lenses and surgery. The compounds of the present invention may be used for the treatment of pain following ocular surgery, such as PRK surgery. With such treatment, the FAAH antagonists can be individually dosed, or in combination with other pharmaceutical agents such as by methods disclosed in U.S. Pat. Nos. 4,939,135 and 5,401,510 (Robertson et al.), the entire contents of which are incorporated herein by reference. The compounds will be utilized in a concentration effective to prevent or ameliorate ocular pain.

The terms "fatty acid amide" and "FAA" include analogs and derivatives thereof. The terms "FAAH antagonist" and "FAAH inhibitor" include any agent that can inhibit the activity of FAAH. FAAs and FAAH inhibitors useful in the methods of the invention include, but are not limited to, oleamide, stearamide, anandamide, lipoaminoacids, ammonium oleoyl-CoA, ammonium arachidononyl-CoA, oleoylglycine, arachidonoylglycine, N-oleoyl-γ-amino-butyric acid, N-oleyl-alanine N-arachidonoyl-γ-amino-butyric acid, N-arachidonoyl-alanine, 2-octoyl γ-bromoacetone, trifluoromethyl ketones, a-keto ester and amides and aldehydes, sulfonyl fluorides, and fluorophosphonates. These agents would be administered at an ophthalmically relevant concentration. As used herein, an "ophthalmically relevant concentration" is less than 5.0% (w/v). FAAH antagonists useful in the methods of the invention include, but are not limited to, FAAH inhibitors described in Boger et al., 2000, *Proc. Natl. Acad. Sci.* 97:5044-5049; Piomelli et al., 2006, *CNS Drug Rev.* 12(1): 21-28; Sit et al., 2007 *Bioorg. Med Chem Lett.* 17: 3287-91; U.S. Pat. No. 6,462,054; U.S. Pat. No. 6,949,574; U.S. Pat. No. 6,562,846; International Patent Application WO 03/065989; International Patent Application WO 04/020430; International Patent Application WO 05/033066; and International Patent Application WO 04/033422; the disclosures of each of which are incorporated by reference in their entirety.

In certain embodiments, an FAAH antagonist may have the following structures described by Boger et al., 2000, *Proc. Natl. Acad. Sci.* 97:5044-5049:

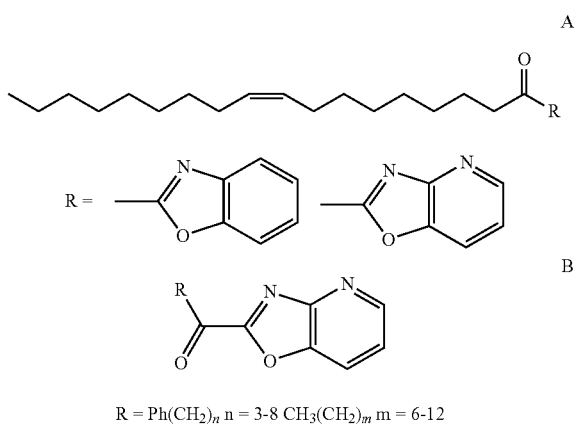

$R = Ph(CH_2)_n$ n = 3-8 $CH_3(CH_2)_m$ m = 6-12

According to the methods of the present invention, a composition comprising one or more of the specified FAAH antagonists or fatty acid amides and a pharmaceutically acceptable carrier for topical ophthalmic administration or implantation into the conjunctival sac or anterior chamber of the eye is administered to a mammal in need thereof. The compositions are formulated in accordance with methods known in the art for the particular route of administration desired.

The compositions administered according to the present invention comprise a pharmaceutically effective amount of one or more of the specified FAAH antagonists or fatty acid amides. As used herein, a "pharmaceutically effective amount" refers to that amount of one or more FAAH antagonists or fatty acid amides that prevents or alleviates ocular pain and/or is sufficient to reduce or eliminate symptoms of dry eye. Preferably, compositions are intended to be administered topically to the eye in the form of eye drops or eye ointments, wherein the total amount of FAAH antagonist or fatty acid amide will be about 0.001 to 5.0% (w/v). Preferably, the amount of FAAH antagonists or fatty acid amides is about 0.01 to about 5.0% (w/v). Preferably, the dosage of an FAAH antagonist used in a method of the invention will be about 200 pM to about 500 µM.

Preferably, the compositions administered according to the present invention will be formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for cytokine synthesis inhibitors which are sparingly soluble in water.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6.0-7.5.

Topical ophthalmic products may also be packaged in multidose form. Preservatives may thus be required to prevent microbial contamination during use. Suitable preservatives include: chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 5.0% w/v. Unit dose compositions of the present invention will be sterile, but typically unpreserved. Such compositions, therefore, generally will not contain preservatives. The ophthalmic compositions of the present invention may also be provided preservative free and packaged in unit dose form.

The preferred compositions of the present invention are intended for administration to a human patient suffering from ocular pain or dry eye or symptoms of dry eye. Preferably, such compositions will be administered topically. In general, the doses used for the above described purposes will vary, but will be in an effective amount to reduce or eliminate ocular pain and/or eliminate or improve dry eye conditions. Generally, 1-2 drops of such compositions will be administered one or more times per day. For example, the composition can be administered 2 to 3 times a day or as directed by an eye care provider.

A representative eye drop formulation is provided in Table 1 below.

TABLE 1

| Ingredient | Amount (% w/v) |
| --- | --- |
| FAAH antagonist or fatty acid amide | 0.001-5.0 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.4 |
| Purified Water | q.s. 100% |

The above composition is prepared by the following method. The batch quantities of boric acid, sodium chloride, disodium edetate, and polyquaternium-1 are weighed and dissolved by stirring in 90% of the batch quantity of purified water. The pH is adjusted to 7.4.+−.0.1 with NaOH and/or HCl. The batch quantity of the FAAH antagonist as a stock solution is measured and added. Purified water is added to q.s. to 100%. The mixture is stirred for five minutes to homogenize and then filtered through a sterilizing filter membrane into a sterile recipient.

All references cited in this application are expressly incorporated by reference herein for any purpose.

Unless otherwise required by context, singular terms used herein shall include pluralities and plural terms shall include the singular.

EXAMPLES

The following examples, including the experiments conducted and results achieved are provided for illustrative purposes only and are not to be construed as limiting the invention.

Example 1

Fatty Acid Amides Decrease Ocular Pain Response

A capsaicin blink test was used to determine the pharmacological effect of two fatty acid amides, oleamide and anandamide. The test measured the pain response of the cornea by the number of times the animal blinked after the application of capsaicin.

Lyophilized anandamide was resuspended in an aqueous 10% cyclodextrin solution that was buffered with an aliquot of 10× phosphate buffered saline (PBS) (Laine et. al., 2001, *Pharmaceutical Research.* 18:494-499). The test article, either cyclodextrin vehicle or fatty acid amide (FAA), was dosed to both eyes of seven week old Sprague-Dawley rats (n=8, per group) five minutes prior to the application of capsaicin. Blinks were counted after the application of anandamide. Animals were dosed with 5 μL of vehicle in OS eye. After a 5-second period, blinks were counted for one minute. Capsaicin (5 μL of 0.0005%) was dosed in the OD eye. Blinks were counted in the same manner as the OS eye.

As shown in FIG. 1, treatment of anandamide on the eyes of Sprague-Dawley rats resulted in a reduced blink rate elicited by capsaicin by 50%. Treatment with anandamide alone resulted in rapid blinking for approximately one minute, followed by normal rates of blinking for the four minutes remaining before capsaicin application. Oleamide showed only a modest decrease (20% reduction) in capsaicin-induced blinking, which is likely due to the only partial solubility of oleamide in the 10% cyclodextrin vehicle. These compounds exhibited the ability to decrease capsaicin-induced blink rates to reduce corneal chemical nociception, thus inhibiting the enzyme that hydrolyzes FAA would allow accumulation of FAAs that decrease pain.

It should be understood that the foregoing disclosure emphasizes certain specific embodiments of the invention and that all modifications or alternatives equivalent thereto are within the spirit and scope of the invention as set forth in the appended claims.

What is claimed is:

1. A non-palliative method for treating dry eye which comprises administering to a mammal a composition comprising a pharmaceutically acceptable carrier and a pharmaceutically effective amount of a fatty acid amide, wherein the fatty acid amide is anandamide.

2. The method of claim 1 wherein the pharmaceutically effective amount of the fatty acid amide is 0.001-5.0% (w/v).

3. The method of claim 1 wherein the pharmaceutically effective amount of the fatty acid amide is 0.01-5.0% (w/v).

4. The method of claim 1 wherein the composition is topically administered to the eye.

5. The method of claim 1 wherein the dry eye is associated with refractive surgery.

* * * * *